(12) United States Patent
McDonell (10) Patent No.: US 11,873,806 B2
(45) Date of Patent: Jan. 16, 2024

(54) PERISTALTIC PUMPS WITH REDUCED PULSATIONS (71) Applicant: Alcon Inc., Fribourg (CH)

(72) Inventor: Brian William McDonell, Irvine, CA (US)

(73) Assignee: Alcon Inc., Fribourg (CH)

( * ) Notice: Subject to any disclaimer, the term of this patent is extended or adjusted under 35 U.S.C. 154(b) by 500 days.

(21) Appl. No.: 17/062,766

(22) Filed: Oct. 5, 2020

(65) Prior Publication Data
US 2021/0100938 A1 Apr. 8, 2021

Related U.S. Application Data (60) Provisional application No. 62/912,120, filed on Oct. 8, 2019.

(51) Int. Cl.
F04B 43/12 (2006.01)
A61M 1/00 (2006.01)
A61F 9/007 (2006.01)
F04B 43/02 (2006.01)
F04B 43/14 (2006.01)
F04B 11/00 (2006.01)

(52) U.S. Cl.
CPC ............ F04B 43/02 (2013.01); A61F 9/007 (2013.01); A61M 1/77 (2021.05); A61M 1/80 (2021.05); F04B 11/0091 (2013.01); F04B 43/12 (2013.01); F04B 43/14 (2013.01)

(58) Field of Classification Search
CPC ...... F04B 43/02; F04B 11/0091; F04B 43/12; F04B 43/14; A61M 1/77; A61M 1/80
See application file for complete search history.

(56) References Cited

U.S. PATENT DOCUMENTS

| | | | |
|---|---|---|---|
| 2,841,091 A * | 7/1958 | Schaurte | F04B 43/14 92/93 |
| 6,261,283 B1 | 7/2001 | Morgan et al. | |
| 6,293,926 B1 | 9/2001 | Sorensen et al. | |
| 6,572,349 B2 | 6/2003 | Sorensen et al. | |
| 6,632,214 B2 | 10/2003 | Morgan | |
| 6,740,074 B2 | 5/2004 | Morgan | |
| 6,902,542 B2 | 6/2005 | Gordon | |
| 6,962,488 B2 | 11/2005 | Davis et al. | |
| 7,393,189 B2 | 7/2008 | Davis et al. | |
| 7,775,780 B2 | 8/2010 | Hopkins | |
| 8,011,905 B2 | 9/2011 | Artsyukhovich | |
| 8,545,198 B2 | 10/2013 | Artsyukhovich | |

(Continued)

Primary Examiner — Connor J Tremarche (57) ABSTRACT

Systems and methods are disclosed for reducing pulsations in peristaltic pumps. In some examples, a cassette comprises a cassette body and a flexible sheet joined to the cassette body, wherein a transition region of the flexible sheet comprises at least one ridge that has a maximum height at a position that is offset from a center line of a cassette body transition channel. In some examples, a cassette body transition channel comprises side walls that taper toward an active region of the fluid path and/or toward a bottom of the transition channel. An example method of operating a peristaltic pump comprises operating rollers at a higher speed during portions of a revolution that otherwise would result in a lower than average flow rate and at a lower speed during portions of the revolution that otherwise would result in a higher than average flow rate.

4 Claims, 8 Drawing Sheets

(56) References Cited

U.S. PATENT DOCUMENTS

| | | | |
|---|---|---|---|
| 8,790,096 B2* | 7/2014 | Sorensen | F04B 43/025 |
| | | | 604/151 |
| 9,482,216 B2 | 11/2016 | Sorensen | |
| 9,931,447 B2 | 4/2018 | Layser | |
| 10,330,234 B1 | 6/2019 | Geschwender | |
| 2010/0049119 A1 | 2/2010 | Norman | |
| 2013/0245599 A1 | 9/2013 | Williams | |
| 2014/0213993 A1 | 7/2014 | Kuebler | |
| 2014/0328697 A1 | 11/2014 | Sorensen | |
| 2016/0166758 A1 | 6/2016 | Norman et al. | |
| 2016/0166785 A1 | 6/2016 | Morrison | |

* cited by examiner

PERISTALTIC PUMPS WITH REDUCED PULSATIONS

TECHNICAL FIELD

The present disclosure is directed to systems and methods relating to peristaltic pumps used, for example, during ophthalmic surgery.

BACKGROUND

In ophthalmic surgical procedures, fluids are often aspirated from the eye during the procedure. For example, in vitreoretinal surgery, a device may be used to aspirate vitreous material from the eye. As another example, in cataract surgery, a device may be used to fragment or emulsify a lens and to aspirate the broken or emulsified lens from the eye.

In addition, in some ophthalmic surgical procedures, it may be desirable to infuse fluid into the eye. For example, in vitreoretinal surgery, cataract surgery, or other procedures, a balanced salt solution (BSS) or other irrigation fluid may be introduced into the eye. The fluid may be removed during the procedure as part of the aspirated fluid.

In such ophthalmic surgical procedures, a peristaltic pump may be used for aspiration and/or infusion of fluid. Peristaltic pumps are a type of positive displacement pump often used in medical devices because of the limited contact between the pump and the fluid. In a typical design, the pumped fluid makes contact only with an easily removable component of the pump system. To achieve flow, the fluid is present in a flexible conduit that is locally collapsed to the point of blocking flow. The sealing point is moved along the conduit in the direction of the flow. To achieve an unlimited flow, this deformation of the conduit is repeatedly produced at multiple locations along the conduit such as by using a set of rollers mounted on a rotating hub with the flexible conduit located adjacent to the rollers.

In some prior systems, a peristaltic pump includes an elastomeric sheet joined to a rigid cassette body, wherein one or more fluid channels are formed in the space between the elastomeric sheet and the cassette body. Rollers mounted on a rotating hub press the elastomeric sheet to produce the pumping action.

Prior systems for fluid aspiration and/or infusion using a peristaltic pump are disclosed in U.S. Pat. Nos. 6,261,283, 6,293,926, 6,572,349, 6,632,214, 6,740,074, 6,902,542, 6,962,488, 7,393,189, 7,775,780, 8,011,905, 8,545,198, 8,790,096, 9,482,216, and 9,931,447, the disclosures of which are hereby incorporated by reference herein in their entirety.

Typically, in a peristaltic pump, the flow is nonconstant with a periodic flow. For example, a flow profile that repeats with the passage of each roller is typical. Prior attempts have been made to reduce pulsations in peristaltic pumps in order to achieve a more stable flow rate. For example, U.S. Pat. No. 6,293,926 discloses an elastomeric sheet having tapered channel transition regions, wherein the channel transition regions of the elastomeric sheet have internal cross-sections that taper from zero to the full cross-section of the channel. U.S. Pat. No. 7,775,780 discloses a cassette body wherein the bottom surfaces of channel transition regions in the cassette are tapered toward the elastomeric sheet to correspond to the shape of the tapered channel transition regions of the elastomeric sheet, in order to provide transition channel regions between the cassette and sheet that have a relatively constant cross-section. U.S. Pat. No. 8,790,096 discloses other designs intended to reduce pulsations, such as a peristaltic pump with two pump conduit segments in which the rollers acting on one pump conduit segment are out of phase with the rollers acting on the other pump conduit segment.

While these prior designs have had some success in reducing pulsations in peristaltic pumps, there is a continuing need for improved designs for reducing pulsations in peristaltic pumps.

SUMMARY

The present disclosure is directed to improved systems and methods for reducing pulsations in peristaltic pumps.

In some example embodiments, a cassette for a peristaltic pump of an ophthalmic surgical system comprises a cassette body and a flexible sheet joined to the cassette body, wherein a transition region of the flexible sheet comprises at least one ridge that has its maximum height at a position that is offset from a center line of a transition channel of the cassette body. The transition region of the flexible sheet may comprise an indentation at a position over the center line of the transition channel of the cassette body. The sheet thickness at the ridge may be greater than the sheet thickness at the indentation.

In some example embodiments, the transition region of the flexible sheet may comprise a plurality of ridges that have their maximum heights at positions that are offset from the center line of the transition channel of the cassette body. The transition region of the flexible sheet may comprise two ridges, each of which has its maximum height at a position that is offset from the center line of the cassette body transition channel. One of the two ridges may be on one side of the indentation, and the other of the two ridges may be on an opposite side of the indentation. The two ridges of the transition region of the flexible sheet may merge into a single ridge in an active region of the flexible sheet.

In some example embodiments, a cassette for a peristaltic pump of an ophthalmic surgical system comprises a cassette body and a flexible sheet joined to the cassette body, wherein a cassette body fluid path transition channel comprises a first end adjacent a port, a second end adjacent an active region, and side walls, and wherein a distance between the side walls tapers toward the second end. In some example embodiments, a distance between the side walls tapers toward a bottom of the cassette body fluid path transition channel.

In some example embodiments, a method of operating a peristaltic pump comprises operating a set of rollers at a speed higher than a nominal speed during portions of a revolution of the set of rollers that would result in a lower than average fluid flow rate if the set of rollers were operated at the nominal speed, and operating the set of rollers at a speed lower than the nominal speed during portions of the revolution of the set of rollers that would result in a higher than average fluid flow rate if the set of rollers were operated at the nominal speed. The set of rollers may be operated in a plurality of compensation cycles, with each compensation cycle going to a speed higher than the nominal speed then to a speed lower than nominal speed. The set of rollers may be operated in a plurality of compensation cycles per revolution of the set of rollers. In some example embodiments, the number of compensation cycles per revolution of the set of rollers may be equal to the number of rollers of the peristaltic pump multiplied by the number of pump segments of the peristaltic pump.

In some example embodiments, the set of rollers is operated in accordance with a compensation profile that determines the speed of the set of rollers. The compensation profile may be a fixed profile or a varying profile. For example, the compensation profile may vary depending on the speed of the set of rollers. The compensation profile may be determined during the operation of the peristaltic pump or prior to the operation of the peristaltic pump. The compensation profile may be associated with indicia located on a removable portion of the peristaltic pump.

These and other examples will be understood by persons having ordinary skill in the art based on this disclosure.

BRIEF DESCRIPTION OF THE DRAWINGS

The accompanying drawings illustrate examples of the systems and methods disclosed herein and, together with the description, serve to explain the principles of the present disclosure.

The accompanying drawings may be better understood by reference to the following detailed description.

DETAILED DESCRIPTION

For the purposes of explaining the principles of the disclosure, reference is made to the drawings, and specific language is used to describe the same. It will nevertheless be understood that no limitation of the scope of the disclosure is intended. Any alterations and further modifications to the described systems, devices, instruments, and methods, and any further application of the principles of the present disclosure, are fully contemplated as would normally occur to one skilled in the art to which the disclosure relates. In particular, the features, components, and/or steps described with respect to one example of the disclosure may be combined with features, components, and/or steps described with respect to other examples of the disclosure. For simplicity, in some instances the same reference numbers are used throughout the drawings to refer to the same or like parts.

FIGS. 1a-1d illustrate a flexible sheet 107 and rigid cassette body 105 as shown in FIGS. 1a-1d of U.S. Pat. No. 8,790,096. The flexible sheet 107 and cassette body 105 may constitute parts of a cassette for a peristaltic pump of an ophthalmic surgical system, for example parts of a cassette as may be used with an ophthalmic surgical console. The term "cassette" as used herein refers to a component of a peristaltic pump that includes a fluid path for the pumping action; the cassette may or may not be removable from the ophthalmic surgical console. The ophthalmic surgical console may be similar to ophthalmic surgical consoles as shown and described in U.S. Pat. No. 9,931,447. The ophthalmic surgical console may be similar to ophthalmic surgical consoles that have been known and used, such as the CONSTELLATION® Vision System available from Alcon Laboratories, Inc. (Fort Worth, Texas) or the CENTURION® Vision System available from Alcon Laboratories, Inc. (Fort Worth, Texas), or any other ophthalmic surgical console suitable for use with the principles described herein.

The ophthalmic surgical console typically includes one or more systems that may be used in performing an ophthalmic surgical procedure. For example, the console typically includes a fluidics system that may include an aspiration system for aspirating fluid from an eye and/or and infusion system for infusing fluid into the eye. The fluidics system may be similar to fluidics systems as shown and described in U.S. Pat. No. 9,931,447, or similar to fluidics systems that have been known and used, such as in the CONSTELLATION® Vision System or in the CENTURION® Vision System, or similar to any other fluidics system suitable for use with the principles described herein.

The sheet 107 and cassette body 105 as shown in FIGS. 1a-1d may constitute parts of a cassette that may be used with the fluidics system of the ophthalmic surgical console. The cassette may be similar to a cassette as shown and described in U.S. Pat. No. 9,931,447, or similar to cassettes that have been known and used, such with the CONSTELLATION® Vision System or the CENTURION® Vision System, or similar to any other cassette suitable for use with the principles described herein. The console may have a set of rollers that are mounted for rotation on a rotary hub. The hub and rollers and cassette (or a portion of the cassette) may together form a peristaltic pump (other components such as a peristaltic pump motor may be included as well).

Figure 1A:
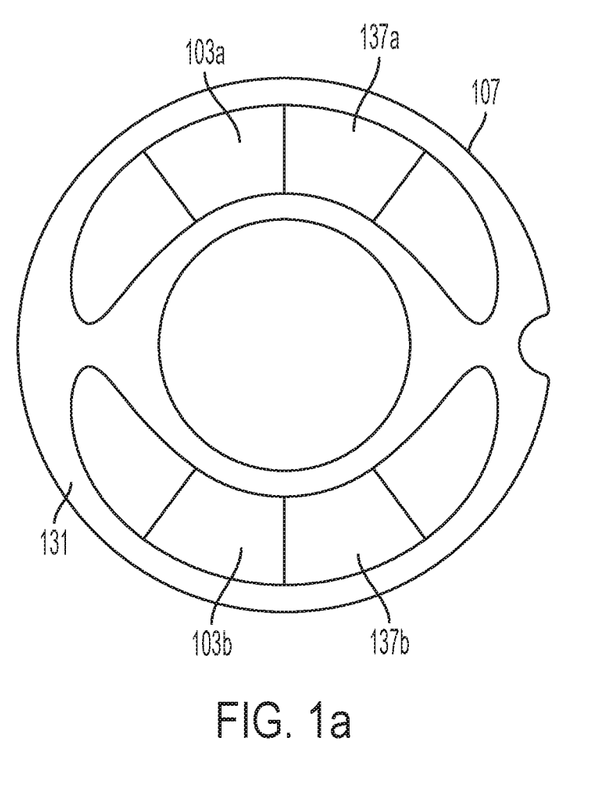
FIG. 1a illustrates a front view of an elastomeric sheet with two pump conduit segments, as disclosed in U.S. Pat. No. 8,790,096.
Figure 1B:
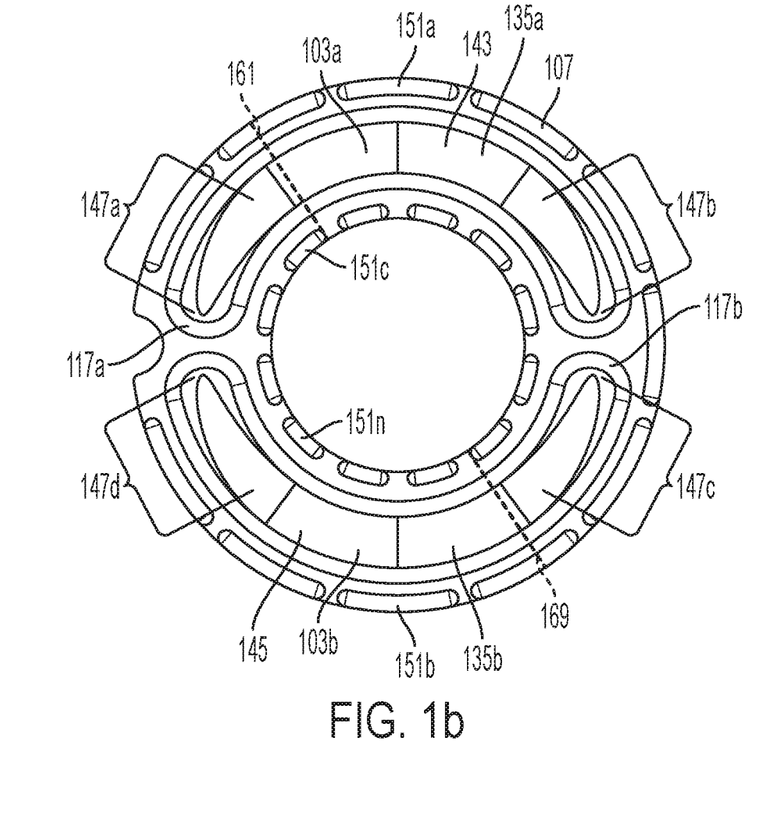
FIG. 1b illustrates a back view of the elastomeric sheet of FIG. 1a, as disclosed in U.S. Pat. No. 8,790,096.

The sheet 107 may be made of a flexible material such as silicone rubber or a thermoplastic elastomer. Other flexible materials may be used. The term "flexible" when used with respect to a sheet as described herein means that the sheet has sufficient flexibility such that it can be deformed for pumping action. The sheet 107 may be one piece or multiple pieces. The sheet may be made by molding or any other suitable method.

Figure 1C:
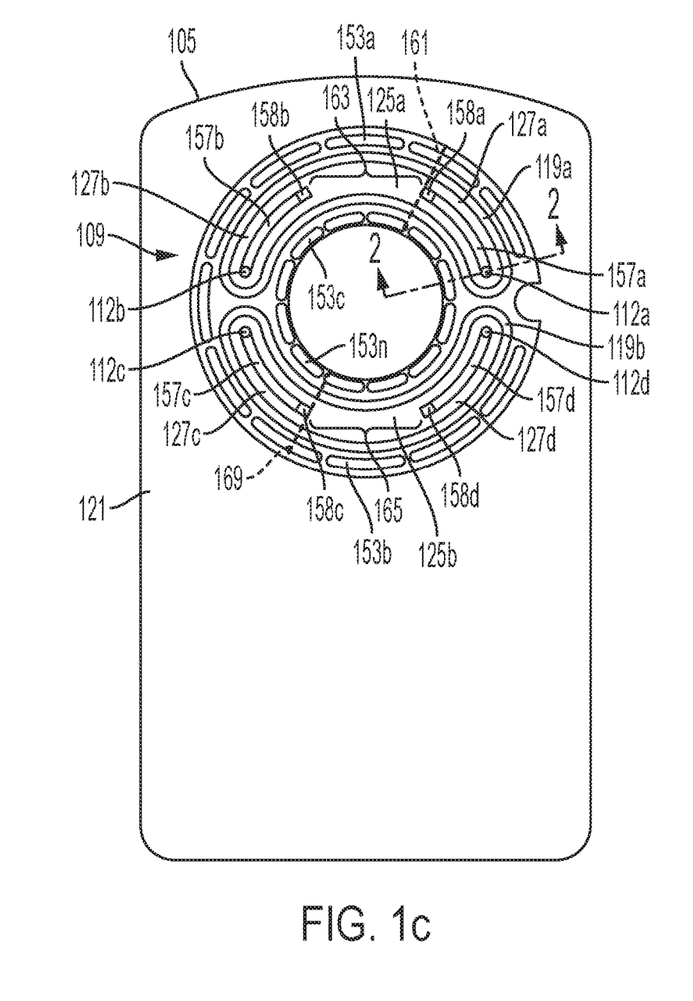
FIG. 1c illustrates a front view of a cassette body with two pump conduit segments, as disclosed in U.S. Pat. No. 8,790,096.
Figure 1D:
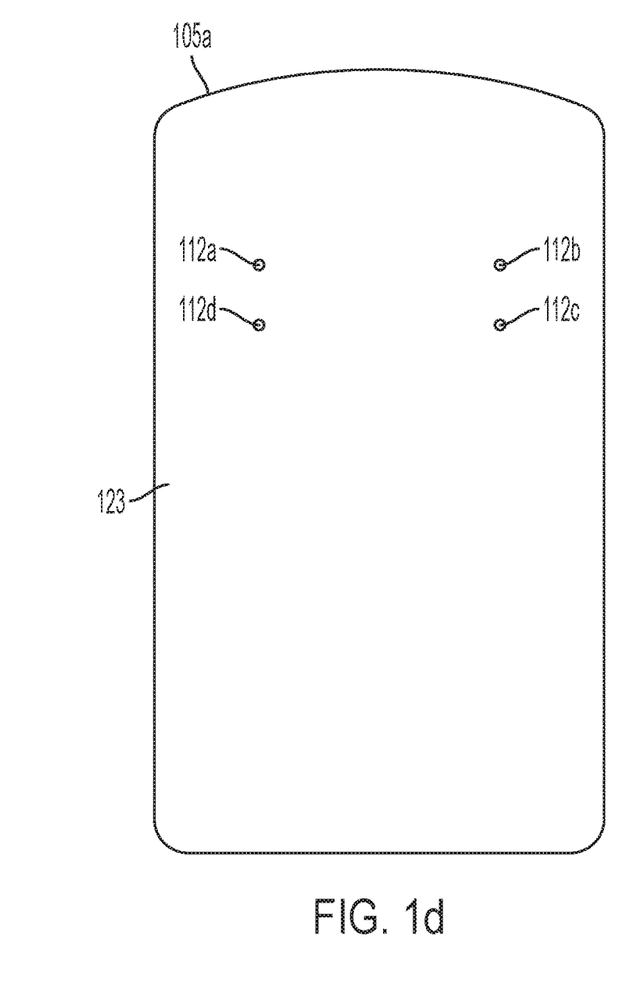
FIG. 1d illustrates a back view of the cassette body of FIG. 1c, as disclosed in U.S. Pat. No. 8,790,096.

The cassette body 105 may be made of a rigid material, such as a rigid thermoplastic material, for example polycarbonate and/or polysulfone, to provide rigidity and structure. The cassette body 105 may be one piece or multiple pieces. The cassette body may be made by injection molding, machining, or any other suitable method. The cassette body 105 may have a pump interface portion which may be engaged by the elastomeric sheet 107 in order to form the pump fluid path, with pump segments of the sheet to be engaged by the pump rollers. Portions of the aspiration flow path and/or infusion flow path may extend as channels and/or tubes inside the cassette body 105.

The cassette body 105 may be provided with holes and/or notches for aligning the cassette with the console when the cassette is loaded into the console. In some examples, the cassette may be a removable and disposable or consumable item that can be used for a single patient procedure. A new cassette may be used for a new procedure.

As described in U.S. Pat. No. 8,790,096, the sheet 107 is adapted to be coupled to the cassette body 105 to define two or more pump fluid paths of the joined sheet 107 and cassette body 105, in the areas designated as sheet pump segments 103a, 103b (collectively, pump segments 103). In some examples, the sheet 107 may be bonded or mechanically attached to the cassette body 105 (e.g., through adhesive, heat fusion, mechanical crimping, rivets, etc.). In some examples, protrusions such as protrusions labeled 151a-n on an outer perimeter and/or interior of the sheet 107 may engage corresponding recesses such as recesses labeled 153a-n on cassette body 105 to connect the sheet 107 to the cassette body 105 and help prevent rotation of the sheet 107 when acted upon by rollers.

As can be seen in FIGS. 1c and 1d, the cassette body 105 has a front surface 121 and a back surface 123. The front surface 121 has a pump interface portion 109 that includes cassette body fluid paths 125a, 125b. Cassette body fluid path 125a comprises an inlet port 112a and an outlet port 112b, a cassette body fluid path active region 163, a cassette body fluid path transition region 127a between the inlet port 112a and the cassette body fluid path active region 163, and a cassette body fluid path transition region 127b between the outlet port 112b and the cassette body fluid path active region 163. Cassette body fluid path 125b comprises an inlet port 112c and an outlet port 112d, a cassette body fluid path active region 165, a cassette body fluid path transition region 127c between the inlet port 112c and the cassette body fluid path active region 165, and a cassette body fluid path transition region 127d between the outlet port 112d and the cassette body fluid path active region 165. Each of the cassette body fluid path transition regions 127a, 127b, 127c, 127d comprises a cassette body fluid path transition channel 157a, 157b, 157c, 157d, respectively, that is recessed with respect to the adjacent cassette body fluid path active region 163 or 165.

As can be seen in FIGS. 1a and 1b, the flexible sheet 107 has a front surface 131 and a back surface 133. The flexible sheet 107 comprises sheet pump segments 103a, 103b. The back surface of each sheet pump segment 103a, 103b defines a sheet fluid path 135a, 135b, respectively. The front surface of each sheet pump segment 103a, 103b comprises a roller engagement surface 137a, 137b, respectively. The sheet pump segment 103a comprises a sheet pump segment active region 143 adapted to be positioned over the cassette body fluid path active region 163, a sheet pump segment transition region 147a adapted to be positioned over the cassette body fluid path transition region 127a, and a sheet pump segment transition region 147b adapted to be positioned over the cassette body fluid path transition region 127b. The sheet pump segment 103b comprises a sheet pump segment active region 145 adapted to be positioned over the cassette body fluid path active region 165, a sheet pump segment transition region 147c adapted to be positioned over the cassette body fluid path transition region 127c, and a sheet pump segment transition region 147d adapted to be positioned over the cassette body fluid path transition region 127d.

In the example of FIGS. 1a-d, protrusions 117a, 117b on the sheet 107 (which may outline the respective sheet fluid paths 135a, 135b) may fit into corresponding recesses 119a, 119b in the cassette body 105 (which may outline the respective cassette body fluid paths 125a, 125b). When the flexible sheet 107 is joined to the cassette body 105, the sheet fluid path 135a is connected with the cassette body fluid path 125a to form a first pump fluid path, and the sheet fluid path 135b is connected with the cassette body fluid path 125b to form a second pump fluid path.

Protrusions 117a, 117b may be secured to the respective recesses 119a, 119b to retain the sheet 107 to the cassette body 105. In some examples, protrusions 151a-n and/or protrusions 117a, 117b may be secured to respective recesses 153a-n and/or recesses 119a, 119b through a mechanical/friction fit, adhesive, heat fusion, etc. In some examples, protrusions 117a, 117b may be secured to respective recesses 119a, 119b to form a seal to prevent escape of a pump fluid from the pump fluid paths.

As described in U.S. Pat. No. 8,790,096, fluid may be pumped through the cassette when a series of rollers engage the two or more pump segments 103a, 103b. The rollers may be radially mounted from an axis of rotation of the peristaltic pump motor (e.g., a stepper or direct current (DC) servo motor, or other motor (such as an alternating current (AC) motor)) and may be configured to compress the pump segments 103 of the sheet 107 against the underlying cassette body 105. The first and second pump fluid paths (125a and 135a, 125b and 135b) may fluidly connect ports in the cassette body 105, e.g., ports 112a, 112b, 112c, 112d (collectively, ports 112). The ports 112a-d may provide respective inlets and outlets for fluid being pumped through the pump fluid paths. As the rollers roll over and away from an inlet port (e.g., inlet ports 112a, 112c), a corresponding fluid bolus may be pulled into the respective pump fluid path (125a and 135a, 125b and 135b) through the inlet port (because of a vacuum created by the roller pushing fluid away from the inlet). As the rollers approach and roll over an exit port (e.g., exit ports 112b, 112d), a corresponding fluid bolus may travel through the exit port.

The two (or more) active pump segments 103 in the sheet 107 may be acted upon by a single hub roller assembly. As rollers engage the pump segments 103, each roller may first roll over a transition region (e.g., transition regions 147a, 147c) with an underlying transition channel (e.g., transition channels 157a, 157c). In some examples, the sheet 107 may not include transition regions 147a-d and the cassette body 105 may not include transition channels 157a-d. As the rollers roll off of a transition region 147a, 147c (and correspondingly, off of a transition channel 157a, 157c), the rollers may form an internal seal within the pump segment 103 (e.g., at point 161 indicated with dashed lines on pump segment 103a or at point 169 on pump segment 103b) by pressing the sheet 107 fully against cassette body 105 at the seal point (in the absence of transition regions and transition channels, the roller may form a seal at the start of the roller's engagement with the sheet 107). The internal seal may move as the roller rolls through the "active" region 163 or 165. As the roller moves, fluid in front of the roller's motion may be pushed through the pump segment 103 resulting in fluid behind the roller's motion being pulled from the inlet (e.g., inlet 112a, 112c). As the next roller on the roller head approaches the transition region 147a, 147c (over transition channel 157a, 157c) behind the roller that is currently forming an internal seal, the next roller may begin to reduce the cross sectional space between the sheet 107 underlying the non-sealed roller and the cassette body 105. Because of the geometry of the transition region 147a, 147c and the underlying transition channel 157a, 157c, the non-sealed roller on the transition region 147a, 147c may have fluid under the roller (e.g., in the transition channel 157a, 157c)

preventing a seal. As the cross-sectional space is reduced (e.g., as the non-sealed roller approaches the seal point or start of the active region 163, 165), fluid being pulled by the sealed roller may slowly be constrained. The fluid flow from the inlet as a result of the sealed active roller may slowly be reduced by the transition roller until the transition roller forms a new seal at the seal point 161 (or 169) and becomes the new active roller (which may effectively isolate the previous sealed roller). The sequence may then be repeated as the next roller on the roller head engages the start of the transition region 147a, 147c (over transition channel 157a, 157c).

The sequence of rollers engaging the transition region 147a, 147c (over transition channel 157a, 157c) and then forming a moving internal seal (with a subsequent roller slowly reducing fluid flow until the subsequent roller forms a seal) may result in cyclical variations (or "pulses") in the fluid flow/pressure profiles of fluid being pulled from the inlet (e.g., inlet 112a, 112c) and/or being pushed to the outlet or exhaust (e.g., outlet or exhaust 112b, 112d).

Figure 2:
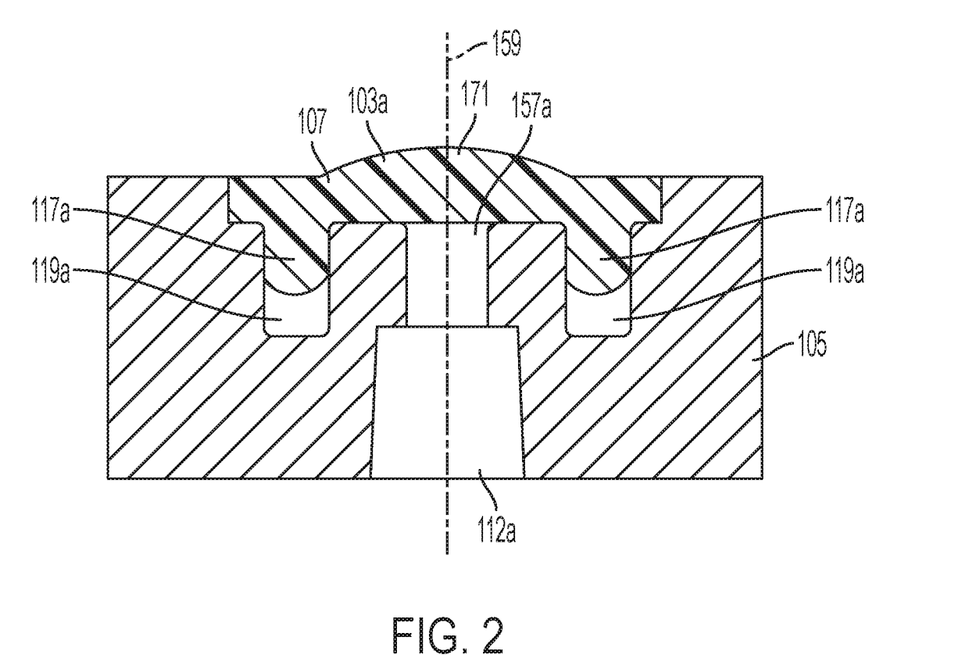
FIG. 2 illustrates a cross-section taken along the line 2-2 in FIG. 1c, showing the cross-sectional view at that plane with the elastomeric sheet of FIGS. 1a-b assembled on the cassette body of FIGS. 1c-d.

FIG. 2 illustrates a cross-section taken along the line 2-2 in FIG. 1c, showing the cross-sectional view at that plane with the sheet 107 of FIGS. 1a-b assembled on the cassette body 105 of FIGS. 1c-d. The protrusions 117a of the sheet 107 can be seen in the recess 119a of the cassette body 105. Line 159 in FIG. 2 marks the center line of the cassette body fluid path transition channel 157a. As can be seen in FIG. 2, the pump segment 103a of the sheet 107 has a raised center portion 171 that is raised over the center of the cassette body fluid path transition channel 157a of the cassette body 105. As the pump segment 103a of the sheet 107 continues from the beginning of the cassette body fluid path transition channel 157a to the beginning of the active region 163, the raised center portion 171 gradually increases in height to a full-height single ridge above active region 163. The raised center portion 171 continues as a full-height single ridge through the active region 163 to the cassette body fluid path transition channel 157b. As the pump segment 103a of the sheet 107 continues from the beginning of the cassette body fluid path transition channel 157b to the outlet 112b, the raised center portion gradually decreases in height. Above outlet 112b, the elastomeric sheet 107 is similar in profile to that shown in FIG. 2 above inlet 112a. The geometry of the pump segment 103b is the same as that of pump segment 103a.

Figure 3:
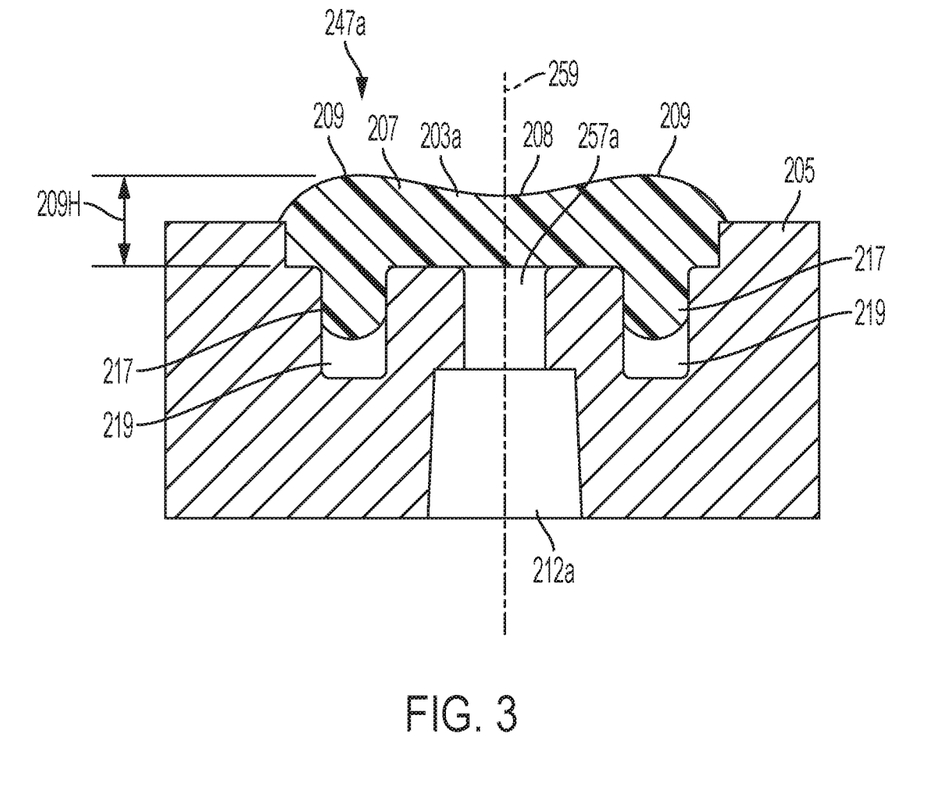
FIG. 3 illustrates a cross-sectional view of a part of a first example of a peristaltic pump in accordance with the disclosure.

FIG. 3 illustrates a cross-sectional view of a part of a first example of a peristaltic pump in accordance with the disclosure. FIG. 3 shows a view similar to that of FIG. 2, with a sheet 207 on a cassette body 205. The cassette body 205 may be similar to and have all of the features of the cassette body 105. The sheet 207 may be similar to and have all of the features of the sheet 107, except that the sheet pump segment transition regions of the pump segments of the sheet 207 have a different profile than the sheet pump segment transition regions 147a-d of the pump segments 103a, 103b of the sheet 107.

As can be seen in FIG. 3, in the area above the inlet 212a, the pump segment 203a of the sheet 207 has a sheet pump segment transition regions 247a with two raised side ridges 209 that are raised on either side of a center portion 208 of the sheet 207, wherein the center portion 208 of the sheet 207 is the portion of the sheet 207 that is above the cassette body fluid path transition channel 257a. The center portion 208 of the sheet 207 is indented with respect to the two raised side ridges 209 on either side of the center portion 208. The center portion 208 comprises an indentation at a position over the center line 259 of the cassette body fluid path transition channel 257a.

As can be seen in FIG. 3, the sheet pump segment transition region 247a comprises at least one ridge 209, in this example two ridges 209, that has its maximum height 209H at a position that is offset from the center line 259 of the cassette body fluid path transition channel 257a. In this example, the height of a point on the sheet 207 represents the height of the front surface of the sheet 207 as measured from a surface of the cassette body 205 that is at the level of the cassette body fluid path active region, resulting in the height 209H for each ridge 209.

The sheet pump segment transition region 247a has a thickness at each ridge 209 that is greater than its thickness at the indentation at the center portion 208. In the example shown, at each ridge 209, the thickness of the sheet 207 extends for the full range of the height 209H of the ridge 209. In other examples, the back surface of the sheet 207 may be raised above the level of the cassette body fluid path active region, such that the thickness of the ridge may be less than the height of the ridge as measured from the level of the cassette body fluid path active region.

The transition region of the flexible sheet 207 may comprise a plurality of ridges that have their maximum heights at positions that are offset from the center line of the transition channel of the cassette body 205. In the illustrated example, one of the two ridges 209 is on one side of the indentation 208, and the other of the two ridges 209 is on an opposite side of the indentation 208. In other examples, other numbers and placements of ridges are possible.

As a pump segment 203a of the sheet 207 continues from the beginning of the cassette body fluid path transition channel 257a at inlet 212a to the beginning of the cassette body fluid path active region (corresponding to active region 163 in FIG. 1c), the raised side ridges 209 gradually decrease in height, until they no longer exist as raised side ridges at the active region. Similarly, as a pump segment 203a of the sheet 207 approaches the beginning of the cassette body fluid path active region (corresponding to active region 163 in FIG. 1c), the indented center portion 208 gradually increases in height, until it becomes the full-sized center region over the cassette body fluid path active region. The sheet pump segment active region of the pump segment 203a (located above the cassette body fluid path active region corresponding to active region 163 in FIG. 1c) has a similar profile to the sheet pump segment active region 143 of the pump segment 103a, with a single raised center portion aligned over the center of the cassette body fluid path active region. As a pump segment 203a of the sheet 207 continues from the beginning of the cassette body fluid path transition channel 257a at inlet 212a to the beginning of the cassette body fluid path active region, the two ridges 209 of the sheet pump segment transition region 247a merge into a single ridge in the sheet pump segment active region.

The trailing transition region of the pump segment 203a from the active region to an outlet is similar to the transition region of the pump segment 203a from the inlet to the active region. From the active region to the outlet, the raised center portion gradually decreases in height until it becomes the indented center portion 208 above the outlet, similar to the indented center portion 208 above the inlet 212a in FIG. 3. Similarly, from the active region to the outlet, the side ridges form and increase in height, until they become the full height of the two raised side ridges 209 as can be seen in FIG. 3.

The sheet 207 has a second pump segment 203b that is similar to the pump segment 103b except that it has the same differences from pump segment 103b as pump segment 203a has from pump segment 103a. The geometry of the pump segment 203b is the same as that of pump segment 203a.

The profile of the elastomeric sheet 207 in FIG. 3 helps reduce pulsations in the peristaltic pump. In the example of FIG. 2, as a roller rolls over an inlet 112a, 112c and transition region, the roller presses the raised center portion 171 downward and into the cassette body fluid path transition channel 157a, 157c, which can cause or contribute to pulsatory flow. Similarly, in the example of FIG. 2, as a roller rolls over a transition region and outlet 112b, 112d, the roller again presses the raised center portion 171 downward and into the cassette body fluid path transition channel 157b, 157d, which can cause or contribute to pulsatory flow. By contrast, in the embodiment of FIG. 3, as a roller rolls over an inlet and transition region, the roller primarily acts against the raised side ridges 209. The raised side ridges 209 and correspondingly indented center region 208 help reduce or eliminate downward protrusion of the center region as the roller passes over the inlet and fluid path transition channel, thereby reducing pulsations in the flow. Similarly, in the embodiment of FIG. 3, a roller rolls from the active region over a transition region and outlet, the roller again primarily acts against the raised side ridges 209. The raised side ridges 209 and correspondingly indented center region 208 help reduce or eliminate downward protrusion of the center region as the roller passes over the fluid path transition channel and outlet, thereby reducing pulsations in the flow. The raised side ridges 209 take pressure off the center region, help prevent the center region from being pushed down into the fluid path transition channel, and accordingly help reduce pulsations in the flow rate.

As an alternative embodiment (not shown) the cassette body 205 could itself be provided with one or more raised shoulders or ramps in the areas of the transition regions. These raised shoulders or ramps could help keep the rollers from pressing as much on the center region of the flexible sheet. Similar to the embodiment of FIG. 3, this would take pressure off the center region of the transition region of the flexible sheet, help prevent the center region of the flexible sheet from being pushed down into the fluid path transition channel, and accordingly help reduce pulsations in the flow rate.

Figure 4:
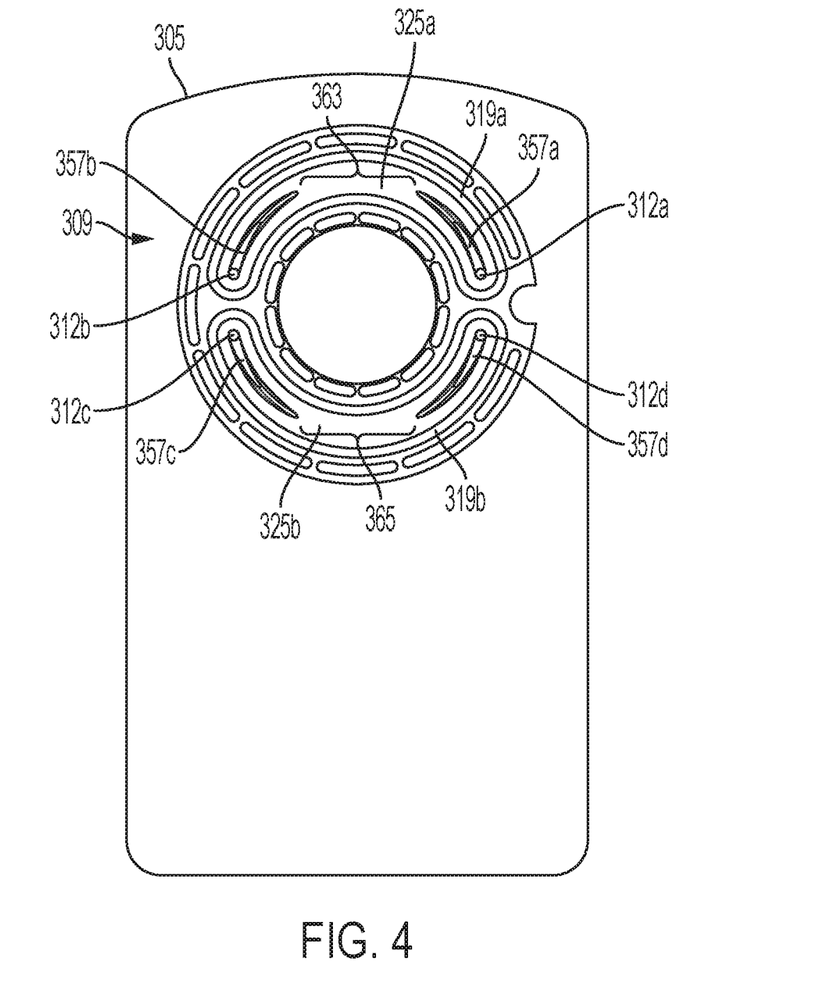
FIG. 4 illustrates a top view of a part of a second example of a peristaltic pump in accordance with the disclosure.

FIG. 4 illustrates a top view of a part of a second example of a peristaltic pump in accordance with the disclosure. FIG. 4 shows a cassette body 305, in a view similar to that of the cassette body 105 in FIG. 1c. The cassette body 305 may be similar to and have all of the features of the cassette body 105, except with respect to the shape of the cassette body fluid path transition channel as shown and as described below. The cassette body 305 may be used with any suitable flexible sheet, such as the sheet 107 or the sheet 207.

The cassette body 305 has a pump interface portion 309 to which an elastomeric sheet (e.g., elastomeric sheet 107 or 207) may be coupled. The pump interface portion 309 has recesses 319a, 319b adapted to receive corresponding protrusions of the elastomeric sheet (e.g., protrusions 117a, 117b). The areas bounded by these recesses 319a, 319b and the corresponding protrusions of the elastomeric sheet constitute the areas for fluid flow within the fluid paths defined in part by cassette body fluid paths 325a, 325b. The fluid flows from inlet 312a to outlet 312b in a first fluid path and from inlet 312c to outlet 312d in a second fluid path.

The cassette body fluid paths 325a, 325b include active regions 363, 365 that are similar to the active regions 163, 165 in FIG. 1b. The pump segments include cassette body fluid path transition channels 357a, 357b, 357c, 357d that are designed to reduce pulsations in fluid flow.

Figure 5:
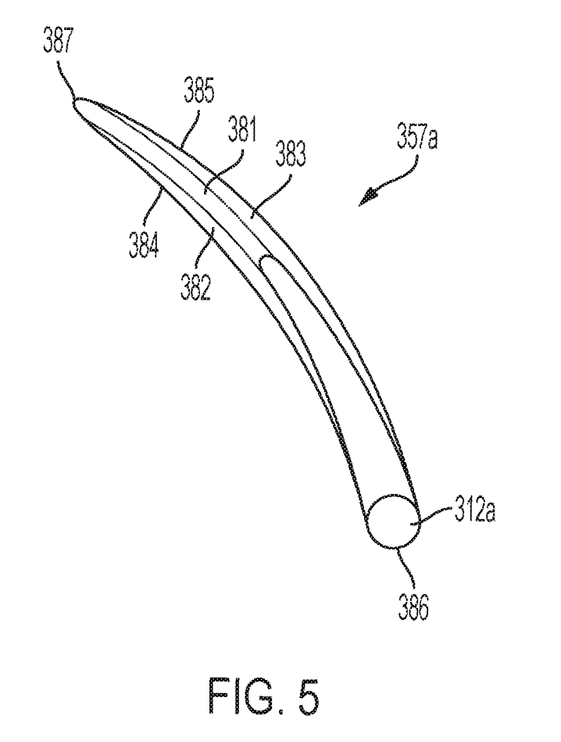
FIG. 5 illustrates an enlargement of a cassette body fluid path transition channel of FIG. 4.

FIG. 5 shows an enlargement of cassette body fluid path transition channel 357a. Transition section 357a includes a bottom surface 381, side walls 382, 383, side wall top edges 384, 385, first end 386 and second end 387. The first end 386 represents the end of the cassette body fluid path transition channel 357a adjacent the inlet 312a, and the second end 387 represents the end of the cassette body fluid path transition channel 357a adjacent the active region 363. The shape of cassette body fluid path transition channel 357a is representative of the shape of the other cassette body fluid path transition channels 357b-d. In the case of a cassette body fluid path transition channel at the end of a pump segment, such as cassette body fluid path transition channels 357b and 357d, the first end 386 represents the end of the cassette body fluid path transition channel 357b, 357d adjacent the outlet 312b, 312d, respectively.

As can be seen in FIGS. 4 and 5, the side walls 382, 383, and the side wall top edges 384, 385, gradually get closer together as they move away from the first end 386 and toward the second end 387 of the cassette body fluid path transition channel 357a. Thus, the width of the cassette body fluid path transition channel 357a gradually gets narrower toward the second end 387 (the width being the dimension across the cassette body fluid path transition channel in a direction along a radius of the pump interface portion). As can be seen in FIGS. 4 and 5, a distance between the two side walls 382, 383 tapers toward the second end 387. In addition, the side walls 382, 383 are sloped such that the side walls 382, 383 are closer together at the bottom surface 381 than they are at the top where they meet side wall top edges 384, 385. As can be seen in FIGS. 4 and 5, a distance between the two side walls 382, 383 tapers toward the bottom 381 of the cassette body fluid path transition channel 357a. The bottom surface 381 also slopes upwardly toward the second end 387. The other cassette body fluid path transition channels 357b-d have the same shape as the cassette body fluid path transition channel 357a.

In prior designs such as the cassette body of FIG. 1c, while having a bottom surface that is sloped upwardly toward the end of the cassette body fluid path transition channels 157a-d (see, e.g., sloped surfaces 158a-d in FIG. 1c), the cassette body fluid path transition channels 157a-d have a constant width at all places across the cassette body fluid path transition channel. By contrast, in the design of FIGS. 4-5, the width of the cassette body fluid path transition channels 357a-d gradually changes, i.e., getting narrower toward the end 387 on account of the side walls 382, 383 (and side wall top edges 384, 385) getting closer together toward the end 387. In addition, due to the slope of the side walls 382, 383, the width of the cassette body fluid path transition channels 357a-d is narrower at the bottom of the cassette body fluid path transition channels 357a-d than at the top.

On account of the geometry as shown in FIGS. 4-5, the fluid flow to and from the active region is smoother and more gradual. The tapering of the side walls 382, 383 both toward the end 387 and toward the bottom 381 of the cassette body fluid path transition channel 357a-d creates a smoother and more gradual flow to and from the active region. This smoother and more gradual flow reduces pulsations in the flow that may be present in prior geometries.

Figure 6:
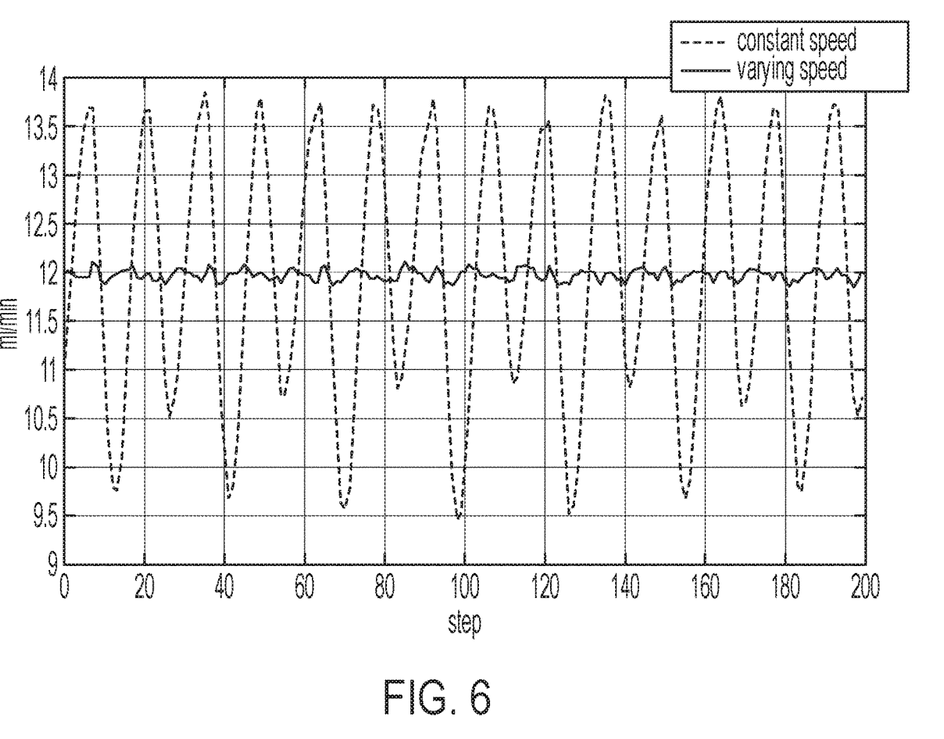
FIG. 6 shows a graph comparing a prior peristaltic pump system operated at a constant speed with a peristaltic pump operated at varying speeds in accordance with the disclosure.

FIG. 6 shows a graph comparing a prior peristaltic pump system at constant speed with a peristaltic pump operated in accordance with the disclosure at varying speeds. The example prior peristaltic pump system in the graph of FIG. 6 (labeled "constant speed") has two pump segments and seven rollers, similar to that described in U.S. Pat. No. 8,790,096. The rollers are operated by a stepper motor, having in this example 200 steps per revolution of the set of rollers. With each revolution of the set of rollers, each roller passes over each of the two pump segments twice. As can be seen in FIG. 6, this example prior system resulted in a pulsed flow ranging from a low of about 9.5 ml/minute to a maximum of about 13.8 ml/minute. The flow went in cycles, with 14 high points and 14 low points, representing the 14 passes of the rollers on the pump segments (7 rollers each passing on 2 pump segments). As can be seen in FIG. 6, every other low point appears different, with one set of low points in the range of about 9.5 ml/minute to about 9.8 ml/minute and the other set of low points in the range of about 10.5 ml/minute to about 10.8 ml/minute, suggesting a difference between the two pump segments.

Figure 7:
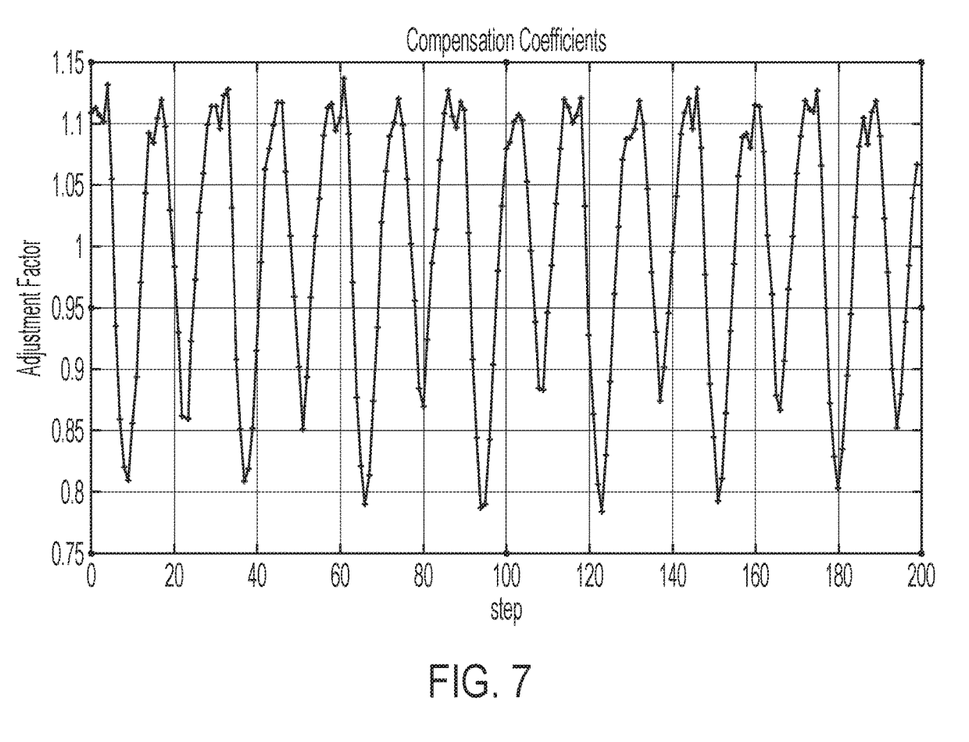
FIG. 7 shows a graph of a compensation profile for operating a peristaltic pump at varying speeds in accordance with the disclosure.

In accordance with this disclosure, the speed of the motor of the peristaltic pump system was modulated based on a measured flow output. The motor was operated faster in areas of measured low flow and slower in areas of measured higher flow. FIG. 7 shows a graph of the speed adjustment factor of the peristaltic pump operated at varying speeds in accordance with the disclosure. Based on the measured flow output, the motor speed was adjusted continuously to speeds between about 0.75 times the nominal operating speed and 1.15 times the nominal operating speed. As can be seen in FIG. 7, the compensation was in cycles reflective of the pulsing flow, with 14 adjustments above nominal speed and 14 adjustments below nominal speed, representing the 14 passes of the rollers on the pump segments (7 rollers each passing on 2 pump segments).

As can be seen in FIG. 6, when operated at varying speeds in accordance with the compensation profile of FIG. 6 (labeled "varying speed" in FIG. 6), the resulting fluid flow was much smoother, with reduced pulsations. This system resulted in a flow in a narrow range around 12 ml/minute+/− 0.2 ml/minute.

A method of operating a peristaltic pump in accordance with the disclosure comprises operating the set of rollers in a rotary manner, such that during each revolution of the set of rollers, each roller makes one revolution around the pump segments; operating the set of rollers at a speed higher than a nominal speed during portions of a revolution of the set of rollers that would result in a lower than average fluid flow rate if the set of rollers were operated at the nominal speed; and operating the set of rollers at a speed lower than the nominal speed during portions of the revolution of the set of rollers that would result in a higher than average fluid flow rate if the set of rollers were operated at the nominal speed. The portions of the revolution during which the set of rollers are operated at a speed higher than a nominal speed do not need to be all portions of the revolution that would result in a lower than average fluid flow rate if the set of rollers were operated at the nominal speed. Similarly, the portions of the revolution during which the set of rollers are operated at a speed lower than a nominal speed do not need to be all portions of the revolution that would result in a higher than average fluid flow rate if the set of rollers were operated at the nominal speed.

The operating of the set of rollers may be performed in a plurality of compensation cycles, with each compensation cycle going to a speed higher than the nominal speed then to a speed lower than nominal speed. The set of rollers may be operated in a plurality of compensation cycles per revolution of the set of rollers. In some embodiments, the number of compensation cycles per revolution of the set of rollers is equal to the number of rollers of the peristaltic pump multiplied by the number of pump segments of the peristaltic pump. For example, in the example of FIGS. 6 and 7, the peristaltic pump has seven rollers and two pump segments, and the compensation cycles per revolution of the set of rollers is fourteen, as can be seen in FIG. 7.

The operating of the set of rollers may performed in accordance with a compensation profile that determines the speed of the set of rollers, such as the compensation profile shown in FIG. 7. The compensation profile may be a fixed profile during the operation of the pump, or it may vary depending on the speed of the set of rollers.

In some embodiments, the compensation profile may be determined during the operation of the peristaltic pump. For example, the flow rate may be measured and the speed of the rollers adjusted in real time. As another example, the flow rate may be measured and the speed of the rollers adjusted based on one or more recent pump cycles. In other embodiments, the compensation profile may be determined prior to the operation of the peristaltic pump. For example, the compensation profile may be determined during testing of the peristaltic pump or during testing of a similar peristaltic pump.

The compensation profile may be associated with indicia located on a removable portion of the peristaltic pump. For example, the cassette may have a bar code or other machine-readable indicia that informs the console of the compensation profile.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A cassette for a peristaltic pump of an ophthalmic surgical system, the cassette comprising:
 a cassette body having a front surface and a back surface, wherein the front surface of the cassette body comprises a cassette body fluid path, wherein the cassette body fluid path comprises a plurality of ports, a cassette body fluid path active region, and a cassette body fluid path transition region between one of the ports and the cassette body fluid path active region, wherein the cassette body fluid path transition region comprises a cassette body fluid path transition channel that is recessed with respect to the cassette body fluid path active region; and
 a flexible sheet joined to the cassette body, wherein the flexible sheet comprises a sheet pump segment with a back surface comprising a sheet fluid path and a front surface comprising a roller engagement surface, wherein when the flexible sheet is joined to the cassette body, the sheet fluid path is connected with the cassette body fluid path to form a pump fluid path, wherein the sheet pump segment comprises a sheet pump segment active region positioned over the cassette body fluid path active region and a sheet pump segment transition region positioned over the cassette body fluid path transition region;

wherein the sheet pump segment transition region comprises at least one ridge on the front surface of the sheet pump segment that has a maximum height at a position that is offset from a center line of the cassette body fluid path transition channel;

wherein the sheet pump segment transition region comprises two ridges on the front surface of the sheet pump segment, each of which has a maximum height at a position that is offset from the center line of the cassette body fluid path transition channel;

wherein the sheet pump segment transition region comprises an indentation at a position over the center line of the cassette body fluid path transition channel;

wherein the sheet pump segment transition region comprises two ridges on the front surface of the sheet pump segment, each of which has a maximum height at a position that is offset from the center line of the cassette body fluid path transition channel;

wherein one of the two ridges is on one side of the indentation, and the other of the two ridges is on an opposite side of the indentation;

wherein the two ridges of the sheet pump segment transition region merge into a single ridge in the sheet pump segment active region.

2. The cassette for the peristaltic pump of the ophthalmic surgical system as in claim 1, wherein the sheet pump segment transition region has a thickness at the at least one ridge that is greater than a thickness at the indentation.

3. The cassette of claim 1, wherein the indentation over the sheet pump segment transition region increases in height until it reaches a full size center region over the cassette body fluid path active region.

4. The cassette of claim 3, wherein the full size center portion decreases in height until it becomes the indentation over the sheet pump segment transition region.

\* \* \* \* \*